United States Patent [19]
Goodman et al.

[11] Patent Number: 6,096,861
[45] Date of Patent: Aug. 1, 2000

[54] PEPTIDE-PEPTOID METAL COMPLEXES

[75] Inventors: Murray Goodman, La Jolla; Elizabeth Jefferson, San Diego, both of Calif.

[73] Assignee: The Regents of the University of California, Oakland, Calif.

[21] Appl. No.: 09/041,145

[22] Filed: Mar. 12, 1998

Related U.S. Application Data

[60] Provisional application No. 60/041,297, Mar. 18, 1997.

[51] Int. Cl.$^7$ .......................... A61K 38/28; A61K 38/16; C07K 5/00; C07K 7/00
[52] U.S. Cl. .......................... 530/304; 530/300; 530/331; 530/332; 530/212; 514/6; 514/18
[58] Field of Search .......................... 514/6, 18; 530/300, 530/304, 331, 332, 212

[56] References Cited

U.S. PATENT DOCUMENTS

| | | |
|---|---|---|
| 5,118,665 | 6/1992 | Pickart . |
| 5,120,831 | 6/1992 | Pickart . |
| 5,164,367 | 11/1992 | Pickart . |
| 5,470,876 | 11/1995 | Procter . |
| 5,538,945 | 7/1996 | Pallenberg et al. . |
| 5,550,183 | 8/1996 | Pickart . |

OTHER PUBLICATIONS

Altura, B.M. (1996) Magnesium–neurohypophyseal hormone interactions in contraction of vascular smooth muscle. Am. J. Physiol. 228(5):1615–1620.

Ananthanarayanan, V.S., Orlicky, S. (1992) Interaction of substance P and its N– and C–terminal fragments with $Ca^{2+}$: implications for hormone action. Biopolymers 32:1765–1773.

Brimble, K.S., Ananthanarayanan, V.S. (1993) Calcium binding and translocation properties of glucagon and its fragments. Biochemistry 32(6):1632–1640.

Di Scala–Guenot, D., Strosser, M. (1992) Oxytocin receptors on cultured astroglial cells. Biochem. J. 284:499–505.

Epand, R.M. (1982) Cation–induced conformational change in glucagon. Mol. Pharmacol. 22:105–108.

Gerega, K., Kozlowski, H., Masiukiewicz, E., Pettit, L.D., Pybum, S., Rzeszotarska, B. (1988) Metal complexes of luteinizing hormone–releasing hormone (LHRH) potentionmetric and.

Goodman, G., Melacini, G., Feng, Y. (1996) Collagen–like triple helices incorporating peptoid residues. J. Am. Chem. Soc, 118:10928–10929.

Gopalakrishnan, V., McNeill, J.R., Sulakhe, P.V. Triggle, C.R. (1988) Hepatic vasopressin receptor: differential effects of divalent cations, guanine nucleotides, and N–ethylmaleimide on agonist and antagonist interactions with the $V^1$ subtype receptor. Endocrinology 123(2):922–931.

Hill, C.P., Dauter, Z, Dodson, E.J., Dodson, G.G., Dunn, M.F. (1991) X–ray structure of an unusual $Ca^{2+}$ site and the roles of $Zn^{2+}$ and $Ca^{2+}$ in the assembly, stability, and storage of the insulin hexamer. Biochemistry 30:917–924.

Kartha, G., Varughese, K.I., Aimoto, S. (1982) Conformation of cyclo(–L–Pro–gly–)$_3$ and its $Ca^{2+}$ and $Mg^{2+}$ complexes. Proc. Natl. Acad. Sci. USA 79:4519–4522.

Madison, V., Atreyi, M., Deber, C.M. Blout, E.R. (1974) Cyclic peptides. IX. conformations of a synthetic ion–binding cyclic peptide, cyclo–(Pro–Gly)$_3$, from circular dichroism and $^1H$ and $^{13}C$ nuclear magnetic resonance. J. Amer. Chem. Soc. 96:21 6725–6734.

Melancini, G., Feng, Y., Goodman, M. (1996) Collagen–based structures containing the peptoid residue N–Isobutylglycine (Nleu). 6. conformational analysis of gly–pro–nleu.

Moehle, K., Hofmann, H. (1996) Peptides and peptoids—a quantum chemical structure comparison. Biopolymers 38:781–790.

Pearlmutter, A.F., Soloff, M.S. (1979) Characterization of the metal ion requirement for oxtocin–receptor interaction in rat mammary gland membranes. J. Biol. Chem. 254(10):3899–3906.

Peggion, E., Mammi, S., Palumbo, M. (1984) Interaction of metal ions with gastrointestinal hormones: binding studies of $Mg^{++}$ to biologically active analogs of little gastrin and minigastrin. Biopolymers 23:1225–1240.

Pliska, V., Kohlhauf Albertin, H. (1991) Effect of $Mg^{2+}$ on the binding of oxytocin to sheep myometrial cells. Biochem. J. 277:97–101.

Seetharama Jois, D.S., Sridhar Prasad, G., Bednarek, M., Easwaran, K.R.K., Vijayan, M. (1993) Structure and conformation of the calcium complex of cyclo(ala–leu–pro–gly)$_2$ in two crystal forms. Int. J. Peptide Protein Res. 41:484–491.

Seetharama Jois, D.S., Easwaran, K.R.K., Bednarek, M., Boult, E.R. (1993) Conformational and ion binding properties of a cyclic octapeptide, cyclo(ala–leu–pro–gly)$_2$. In. J. Peptide.

Varughese, K.I., Aimoto, S., Kartha, G. (1986) Calcium binding cyclic hexapeptide. Int. J. Peptide Protein Res. 27:118–122.

Williams, P.F., Caterson, I.D., Cooney, G.J., Zilkens, R.R., Turtle, J.R. (1990) High affinity insulin binding and insulin receptor–effector coupling: modulation by $Ca^{2+}$. Cell Calcium 11:547–556.

Jefferson et al., *J. Am Chem Soc.,* vol. 119, No. 13, pp 3189–3190, 1997.

*Primary Examiner*—Avis M. Davenport
*Attorney, Agent, or Firm*—Pillsbury, Madison & Sutro, LLP; Anita M. Kirkpatrick

[57] ABSTRACT

A chemical complex comprising divalent metal ions, preferably $Ca^{+2}$ ions, and peptide-peptoid trimers in a fixed ratio and having a centrosymmetric crystalline structure wherein three divalent metal ions at the interior of the complex are coordinated with the peptide carboxylate and urethane oxygen atoms. The globular complex has a hydrophobic outer surface and is useful as an ionophore.

22 Claims, 3 Drawing Sheets

PEPTIDE-PEPTOID METAL COMPLEXES

This application claims priority to U.S. provisional application Ser. No. 60/041,297, filed Mar. 18, 1997.

Certain aspects of the invention disclosed were made with the support, in part, of a National Science Foundation Grant (NSFDMR-9201133). The United States government may have certain rights in the invention.

The invention relates to chemical complexes comprising peptides and divalent metal ions. Particularly it relates to multinuclear $Ca^{2+}$ complexes of linear N-protected peptide derivatives comprising peptoid residues.

BACKGROUND OF THE INVENTION

Divalent cations such as $Mg^{2+}$ or $Ca^{2+}$ are known to be important in modulating the binding affinity of hormones such as oxytocin (Di Scala-Guenot, D. et al., *Biochem. J.* 284:499–505, 1992; Pearlmutter, A. F. et al. *J. Biol. Chem.* 254:3899–3906 1979; Pliska, V., et al. *Biochem. J.* 277:97–101, 1991); vasopressin (Di Scala-Guenot, D. et al., 1992; Pearlmutter, A. F. et al., 1979; Altura, B. M. et al. *Am. J. Physiol.* 228:1615–1620, 1996; and Gopalakrishnan, V. et al. *Endocrinology* 123:922–930, 1988); gastrin (Peggion, E. et al. *Biopolymers* 23:1225–1240, 1984); glucagon (Epand, R. M. *Mol. Pharmacol.* 22:105–108, 1982; and Brimble, K. S. et al. *Biochemistry* 32:1632–164, 1993); GnRH (Gerega, K. et al. *J. Inorg. Biochem.* 33:11–18, 1988); insulin (Hill, C. P. et al. *Biochemistry* 30:917–924, 1991); substance P (Ananthanarayanan, V. S. et al. *Biopolymers* 32:1765–1773, 1992); and bombesin (Saint-Jean, A., et al., Poster presentation at the 13th *American Peptide Symposium*, Edmonton, Canada, 1993). The cell receptors of these hormones are also known to bind $Ca^{2+}$ (Williams, P. F. et al. *Cell Calcium* 11:547–556, 1990. Synthetic peptide-metal complexes are potentially useful in methods for intracellular delivery of these cations.

To date, only two crystal structures of synthetic $Ca^{2+}$-complexes with peptides have been reported and both of these crystal structures are of cyclic peptides (Seetharama Jois, D. S. et al. *Int. J. Peptide Protein Res.* 41:484–491, 1993 and Varughese, K. I. et al. *Int. J. Peptide Protein Res.* 27:118–122, 1986. In $c(Ala-Leu-Pro-Gly)_2.Ca(ClO_4)_2$ (Seetharama Jois, D. S. et al., 1993), complexation occurs through an incomplete encapsulation of the metal ion by the peptide molecule, and in $c(Pro-Gly)_3.Ca(ClO_4)_2$ (Varughese, K. I. et al., 1986), a complete encapsulation is found wherein two cyclic peptide molecules sandwich a $Ca^{2+}$ ion. Solvent molecules occupy coordination sites in both of these crystal structures. Complexation of linear peptides to $Ca^{2+}$ cations in solution has been studied by a variety of techniques, such as CD, NMR, and IR spectroscopies. It is desirable to synthesize other types of linear metal-peptide complexes having biologically useful applications.

SUMMARY OF THE INVENTION

According to the invention there is provided a chemical complex comprising three divalent metal ions independently selected from the group consisting of $Ca^{2+}$, $Mg^{2+}$, $Fe^{2+}$ and $Mn^{2+}$ and six linear, N-protected peptide-peptoid trimers. In one embodiment the chemical complex comprises three divalent metal ions selected from the group consisting of $Ca^{2+}$, $Mg^{2+}$, $Fe^{2+}$ and $Mn^{2+}$ coordinated to six linear, N-protected peptide-peptoid trimers wherein solvent molecules are not bound at the coordination sites. In a preferred embodiment the chemical complex comprises at least two species of linear N-protected peptide-peptoid trimers.

According to one aspect of this embodiment the peptoid residues of the chemical complex are N-substituted isomers of amino acids selected from the group consisting of glycine, valine, leucine, isoleucine, glutamine, lysine, phenylalanine and aspartic acid. Particularly the N-protected peptide-peptoid trimer is a Boc-Gly-AA-peptoid, a Boc-Gly-peptoid-AA or a Boc-Gly-dipeptoid, wherein the peptoid is selected from the group consisting of N-substituted isomers of glycine, valine, leucine, isoleucine, glutamine, lysine, phenylalanine, and aspartic acid.

According to another aspect of this embodiment the chemical complex comprises three divalent metal ions independently selected from the group consisting of $Ca^{2+}$, $Mg^{2+}$, $Fe^{2+}$ and $Mn^{2+}$ and six linear, N-protected Gly-dipeptoid trimers. In a preferred aspect of this embodiment the peptide-dipeptoid trimers are Gly-Nleu-Nleu.

According to yet another embodiment of the invention the chemical complex comprises three divalent metal ions independently selected from the group consisting of $Ca^{2+}$, $Mg^{2+}$, $Fe^{2+}$ and $Mn^{2+}$ and six linear, N-protected dipeptide-peptoid trimers. The dipeptide-peptoid trimers are Gly-Pro-Nleu or Gly-Nleu-Pro.

In a preferred aspect of this embodiment the chemical complex comprises N-protected dipeptide-peptoid trimers selected from the group consisting of Boc-Gly-Pro-Nleu-O⁻

Boc-Gly-Nleu-Pro-O⁻

Boc-Gly-AA-Nleu-O⁻; and

Boc-Gly-Nleu-AA-O⁻ wherein AA is any selected substituted or unsubstituted α-amino acid residue whether naturally occurring or synthetic. For example, the chemical complex can be of the formula $Ca^{2+}_3(Boc-Gly-Pro-Nleu-O^-)_6$ or $Ca^{2+}_3(Boc-Gly-Nleu-Pro-O^-)_6$. For example, the chemical complex can have the formula $M^{2+}_3 (Boc-Gly-Nleu-Nleu-O)_6$, wherein $M^{2+}$ is a divalent metal ion selected from the group consisting of $Ca^{2+}$, $Mg^{2+}$, $Fe^{2+}$ or $Mn^{2+}$ and Nleu is N-isobutylglycine. Particularly the calcium complex can have the formula $Ca^{2+}_3(Boc-Gly-Nleu-Nleu-O)_6$, wherein Nleu is N-isobutylglycine.

According to yet another aspect of the invention the chemical complex has a globular centrosymmetric conformation, comprising three divalent metal ions and six N-protected peptide-peptoid trimers, wherein said divalent metal ions are in the central core of the globular complex, and the anionic carboxylate regions of said N-protected peptide-peptoid trimers face inwardly and the hydrophobic portions of said N-protected peptide-peptoid trimers face outwardly.

In a preferred aspect of this embodiment, the chemical complex has a globular centrosymmetric conformation, comprising three $Ca^{++}$ ions and six N-protected peptide-peptoid trimers, wherein said calcium ions are in the central core of the globular complex, and the anionic carboxylate regions of said N-protected peptide-peptoid trimers face inwardly and the hydrophobic portions of said N-protected peptide-peptoid trimers face outwardly. Particularly, according to this aspect of the invention there is provided a chemical complex according to wherein one of said calcium ions is located at the center of symmetry and two of said calcium ions are located lateral thereto, and said central calcium ion is coordinated to six peptide-peptoid trimers through C-terminal carboxylate oxygens thereof and each said lateral calcium ions is coordinated to three of said peptoid-peptide trimers both through a carboxylate oxygen and a urethane oxygen thereof. In preferred aspects of this embodiment the chemical complex the six trimers are Boc-Gly-Nleu-Nleu-O and each trimer is coordinated to a lateral calcium ion through a first carboxylate oxygen and a urethane carbonyl oxygen and each said trimer is coordinated to the central calcium ion through a second carboxylate ion. Particularly the chemical complex has the formula $Ca^{2+}_3$ $(Boc-Gly-Nleu-Nleu-O)_6$, wherein Nleu is N-isobutylglycine. In one embodiment, the chemical complex can be globular complex wherein one side of the globular complex consists of structures of left-handed helicity and the opposite side consists of structures of right-handed helicity.

According to another aspect of the invention there is provided a chemical complex wherein the N-protecting group is a hydrophobic moiety selected from the group consisting of $C_6-C_{24}$ alkyl groups, aromatic groups such as benzyl and conventional peptide blocking groups such as t-butyloxycarbonyl (tBoc), benzyloxycarbonyl, biphenylylisopropyloxycarbonyl (Bpoc), triphenylmethyl (trityl), 9-fluorenylmethyloxycarbonyl (Fmoc) and p-toluenesulfonyl groups. In a preferred embodiment of the invention, the side chains of the residues in each said linear N-protected peptide-peptoid trimer are achiral. Alternatively, the side chains of the residues in each said linear N-protected peptide-peptoid unit are chiral.

The advantage of the calcium-binding ligands is the simplicity of the ligand per se. The ligand is a peptide-dipeptoid trimer and the overall structure is achiral. There is no involvement of solvent ions in the X-ray crystal structure which suggests that the Boc-Gly-Nleu-Nleu-O⁻ complex is a good calcium binder. In addition, since the ligands contain peptoid units, it is expected to be biostable. The $Ca^{2+}_3$ $(Boc-Gly-Nleu-Nleu-O^-)_6$ complex has a hydrophobic periphery which suggests that is may be able to traverse a lipid membrane. The complex therefore serves as a model for the design of ionophores which can introduce metal cations into cells and organelles. Ionophores also have therapeutic potential since they have the ability to alter membrane permeability.

DETAILED DESCRIPTION OF THE PREFERRED EMBODIMENT

We have discovered that N-protected linear peptide-peptoid trimers can be ligands for small divalent metal ions, forming a complex in which the metal ions are tightly bound and solvent molecules such as $H_2O$ are absent from the coordination sites.

The present invention is related to recently disclosed building blocks for collagen-like structures comprising peptidomimetic residues such as N-isobutylglycine (Nleu) (Melancini, G.; Feng, Y.; Goodman, M. *J. Am. Chem. Soc.* 1996, 118, 10725–10732; and Goodman, G.; Melacini, G.; Feng. Y. *J. Am. Chem. Soc.* 1996, 118, 10928–10929) and the synthesis of peptide-peptoid oligomers. The preparation and properties of these structures is disclosed in application Ser. No. 08/668,360 which is hereby incorporated by reference in its entirety. The structure of the peptoid residues in the linear peptide-peptoids of the invention can be any N-substituted amino acid with a hydrophobic R (side chain) group. That is, the peptoid may contain R groups that are hydrophobic side chains of amino acids (AA) or the R group could be any aliphatic chain or aromatic-containing side chain. Included within the scope of the invention are peptide-peptoid divalent metal binding ligands wherein the side chains of the peptide or peptoid residues are chiral or achiral. The metal ion can be any small divalent ion such as, for example, $Fe^{+2}$, $Ca^{+2}$ or $Mg^{+2}$. The preferred ions are $Mg^{+2}$ and $Ca^{+2}$.

The peptoid residues of the trimers may be any N-substituted isomer of an amino acid, for example, glycine, valine, leucine, isoleucine, glutamine, lysine, phenylalanine or aspartic acid. The amino acid residue can be any substituted or unsubstituted α-amino acid residue whether naturally occurring or synthetic. The ligands also include not only peptide-dipeptoid trimers, but also dipeptide-peptoid trimers having a single peptoid residue. The peptide-peptoid trimers complexed with the metal ions may have identical or different peptide-peptoid sequences.

Preferably, the N-terminal blocked residue is glycine (Gly). For example, the invention includes the preferred blocked trimers:

Boc-Gly-peptoid-peptoid-O⁻

Boc-Gly-peptoid-AA-O⁻

Boc-Gly-AA-peptoid-O⁻

Particularly preferred blocked trimers are:

Boc-Gly-Pro-Nleu-O⁻

Boc-Gly-Nleu-Pro-O⁻

Boc-Gly-AA-Nleu-O⁻; and

Boc-Gly-Nleu-AA-O⁻ wherein AA is any selected α-amino acid residue whether naturally occurring or synthetic. Preferably the amino acid residue is proline.

The N-blocking group can be any hydrophobic moiety known to peptide chemists for blocking terminal amino groups of amino acids and peptides during solid phase peptide synthesis. Examples of suitable groups are for example, hydrophobic moieties selected from the group consisting of long chain $C_6-C_{24}$ alkyl groups, aromatic groups such as benzyl, other complex groups bearing aromatic structures, as well as the conventional peptide blockers known to be useful, such as t-butyloxycarbonyl (tBoc), benzyloxycarbonyl, biphenylylisopropyloxycarbonyl (Bpoc), triphenylmethyl (trityl), 9-fluorenylmethyloxycarbonyl (Fmoc) and p-toluenesulfonyl groups. The N-blocking group is preferably a conventional tert-butyloxycarbonyl group.

As part of these studies Boc-Gly-Nleu-Nleu-OH (I) was synthesized and it was discovered that its ionized form complexes calcium ions. Accordingly, a preferred embodiment of the invention comprises a calcium complex of a linear peptide-like molecule and its crystalline structure. The structure of $Ca^{2+}_3$ (Boc-Gly-Nleu-Nleu-O⁻)₆, where Nleu denotes N-isobutylglycine, was determined by single crystal X-ray diffraction techniques. The calcium ions are completely encapsulated through the oxygen atoms of the N-protected glycyl-dipeptoid derivative, without any involvement of solvent molecules. The urethane and the two peptoid amide bonds of the glycyl dipeptoid molecule are in a trans, cis, and cis conformation, respectively.

(I)

Figure 2:
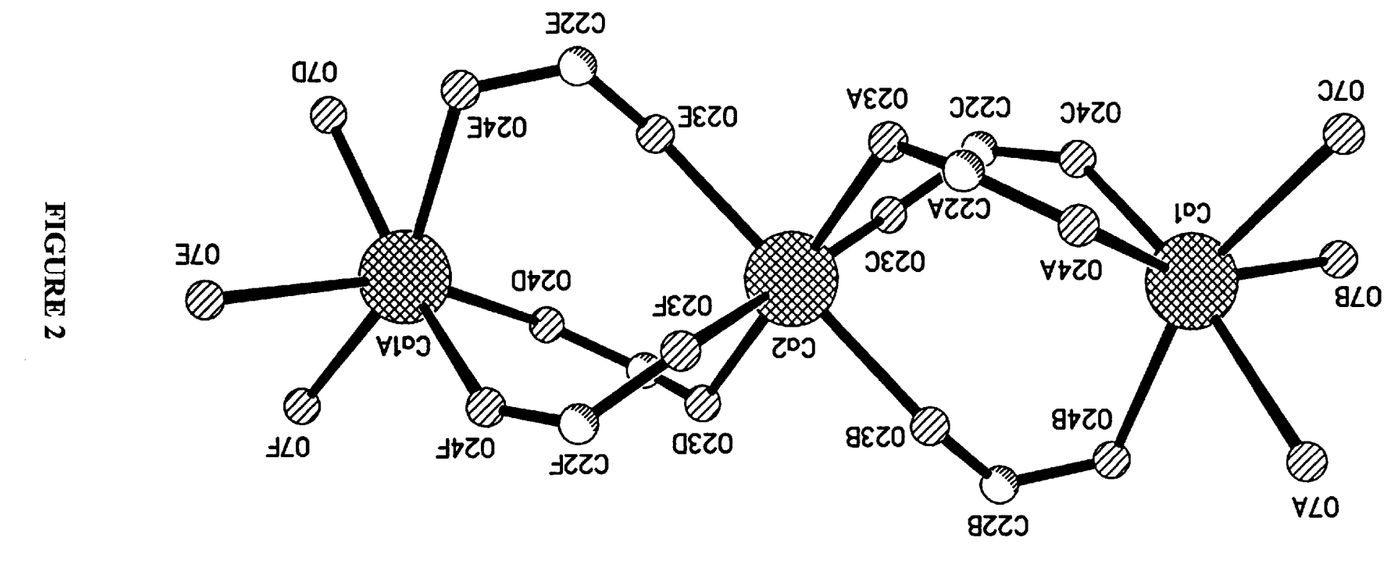
FIG. 2 shows the coordination of the oxygen atoms of the peptide-peptoid units to $Ca^{2+}$ ions.
Figure 3:
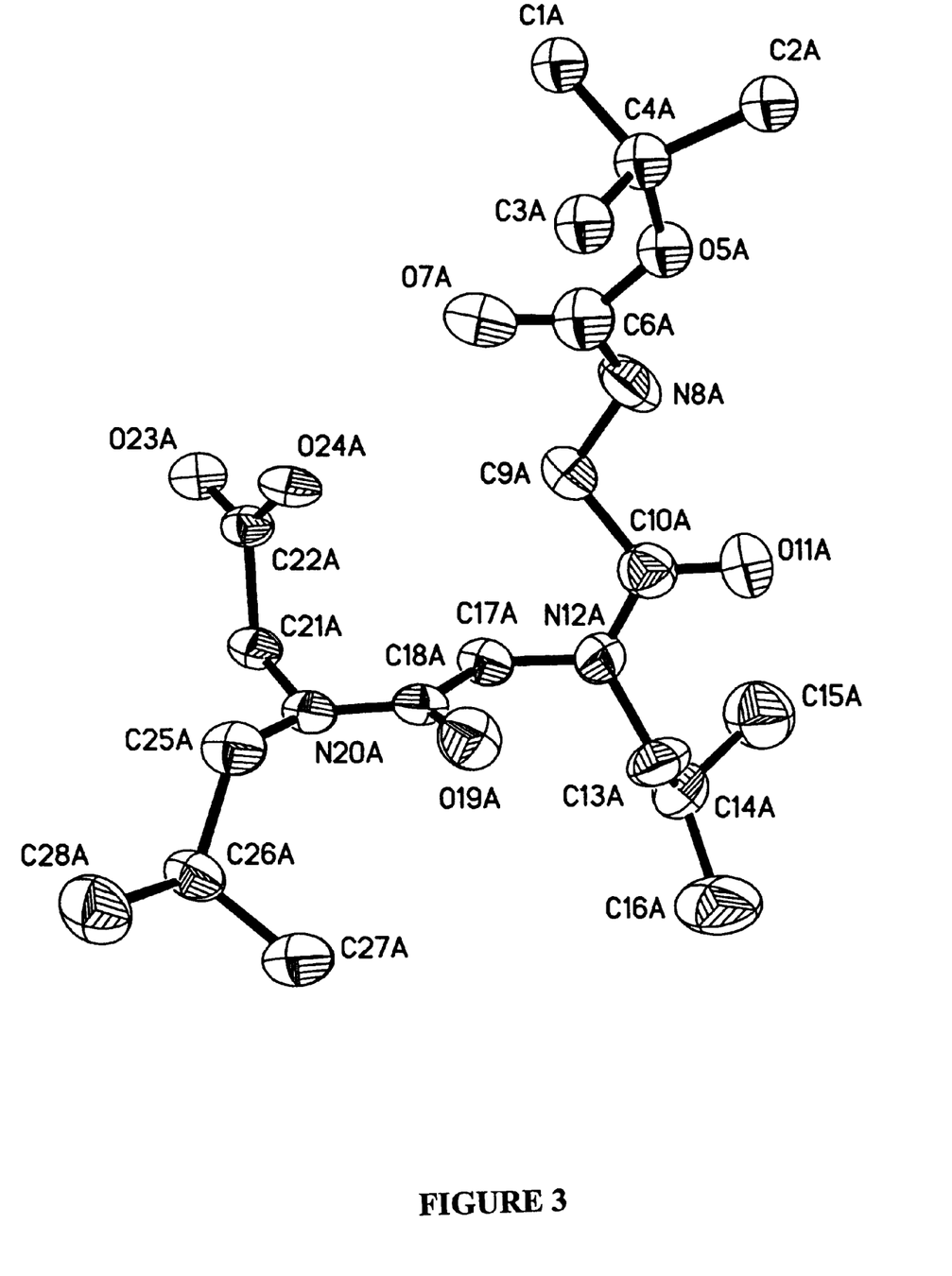
FIG. 3 shows the structure of the Boc-Gly-Nleu-Nleu-O⁻ unit.

The structure of $Ca^{2+}{}_3(Boc\text{-}Gly\text{-}Nleu\text{-}Nleu\text{-}O^-)_6$ (FIG. 1) was determined by single crystal X-ray diffraction techniques as described in the Experimental section. The calcium cations are completely encapsulated through oxygen atoms of the N-protected glycyl-dipeptoid derivative (FIG. 2) without any involvement of solvent molecules, although they are present in the unit cell. The experimental data also describes an extensive analysis of the conformation of the Nleu peptoid residue. The conformation of the glycyl-dipeptoid molecule is presented in FIG. 3.

Figure 1:
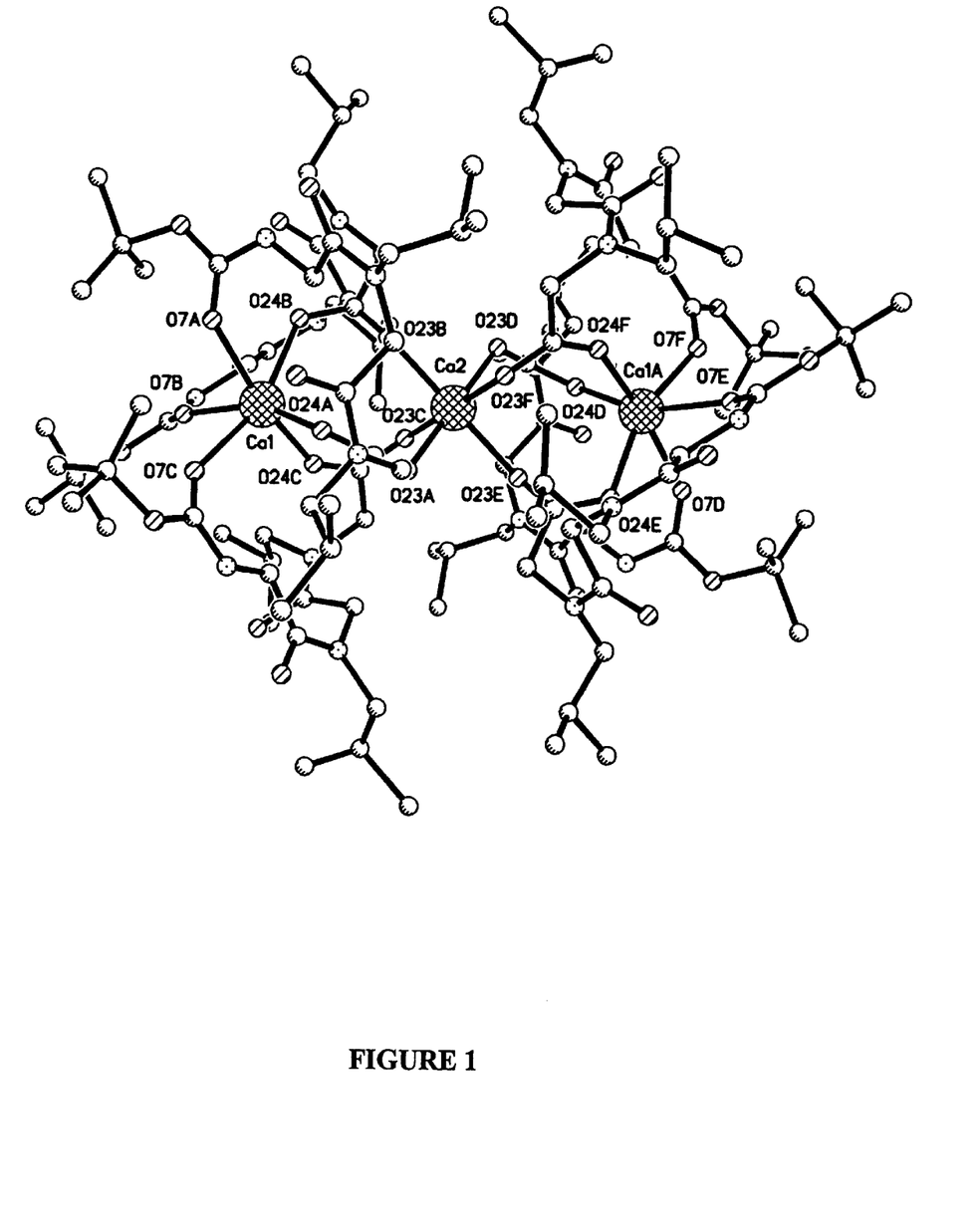
FIG. 1 shows the structure of the $Ca^{2+}_3$ (Boc-Gly-Nleu-Nleu-O)₆ entity, where Nleu is N-isobutylglycine. Calcium ions and oxygen atoms are represented as hatched and crossed circles, respectively. The central calcium ion is positioned on a center of symmetry.

In $Ca^{2+}{}_3$ $(Boc\text{-}Gly\text{-}Nleu\text{-}Nleu\text{-}O^-)_6$, each glycyl-dipeptoid unit occupies a folded conformation and behaves as a bischelate toward a lateral calcium ion. The folding of the backbone chain, which results in coordination to the divalent cation, is made possible because of the cis conformation of the two tertiary amide linkages involving Nleu peptoid residues. All six independent N-protected trimer molecules have nearly the same conformation and the C-terminal groups exist as carboxylate anions in the crystal structure. Each trimer molecule acts as a bidentate ligand toward one lateral calcium cation, which coordinates one oxygen of the carboxylate group as well as the urethane carbonyl oxygen. The coordination at the bivalent ion resembles an octahedral complex. The trimer units are able to complex the central calcium ion through their second carboxylate oxygens. The central calcium ion is therefore coordinated to all six glycyl-dipeptoid units. The central calcium ion sits on the center of symmetry so that the resulting globular entity is centrosymmetric with one half of it consisting of structures of right-handed helicity and the other half consisting of structures of left-handed helicity. This arrangement is made possible because of the achiral nature of the three residues in each peptoid containing trimer. The globular entity, $Ca^{2+}{}_3(Boc\text{-}Gly\text{-}Nleu\text{-}Nleu\text{-}O^-)_6$, is rather hydrophobic on the surface where the methyl groups of the Boc termini and the isobutyl side chains are located. In the central core of the globular complex all of the charged carboxylate oxygen atoms are positioned. The central $Ca^{2+}$ ion on the average shows Ca-O distances of 2.20 Å, while the lateral $Ca^{2+}$ ion shows Ca-O distances of 2.35 Å and 2.38 Å with carboxylate and carbonyl oxygens, respectively.

The three independent achiral molecules coordinated to the lateral calcium ions have very similar conformational angles $\phi,\psi$ and $\omega$: $Gly^1$ ($\approx 180°$, $\approx 180°$, $\approx 0°$), $Nleu^2$ and $Nleu^3$ residues ($\approx -70°$, $\approx 180°$, $\approx 0°$) corresponding to right handedness. The centrosymmetric related molecules on the other side of the central calcium ion have opposite handedness with opposite conformational angles. The urethane and the two amide bonds along the chain are in a trans, cis, and cis conformation, respectively, with considerable deviation from planarity. Four of the six side chains of the independent Nleu peptoid residues have $\chi^1$ and $\chi^2$ values near $-110°$, $60°$ (and 180°) while the remaining two exhibit the opposite values: 110°, 60° (and 180°). The observed conformation of the Nleu peptoid residues corresponds to the minimum energy conformation cis $\alpha_D$ form found by others in ab initio calculations (Moehle, K., et al.(1996) *Biopolymers* 38:781–790. The trans conformation of the $\phi$ and $\psi$ angles allows for the onset of the intramolecular N—H . . . C=O hydrogen bond between the N—H and the C=O groups of the Gly residue ($C_5$-conformation), which are not involved in other intermolecular H-bond interactions. Hydrophobic intermolecular interactions allow for the packing of the $Ca^{2+}{}_3\{Boc\text{-}Gly\text{-}Nleu\text{-}Nleu\text{-}O^-\}_6$ globular entities in the crystal.

The calcium complexing ligand was prepared by reacting Boc-Gly-Nleu-OH with Nleu-OEt using BOP (O-benzotriazolyl-N-oxytri-dimethylamino-phosphonium hexafluorophosphate) as the activating reagent to give Boc-Gly-Nleu-Nleu-OEt (Scheme 1). The trimer was then saponified with KOH in $H_2O$ (containing calcium ions)-THF to afford the calcium complex of Boc-Gly-Nleu-Nleu-OH. The calcium ions in the water were sufficient to form the complex. Calcium complexing ligands containing other peptide-peptoid trimers can be prepared in the same manner by substituting the appropriate amino acid or peptoid molecule.

The particularly preferred peptoid-containing calcium ligand, Boc-Gly-Nleu-Nleu-O$^-$, has a comparatively simple structure when compared to other calcium-binding peptides. The binding of peptoid-containing peptides to calcium is also not previously known. Because no solvent molecules coordinate with the calcium ion in the complex, the peptide-peptoid ligand appears to be extremely effective at binding calcium ions. It is believed that the cis configuration of the two peptoid amide bonds facilitates this chelation to calcium.

Other small divalent metal ions having about the same diameter as calcium are expected to complex with analogous peptide-peptoid trimers having similar physical characteristics in substantially the same structures and having the same proportion of peptide to metal compositions.

Experimental

The preparation of the compounds of the present invention is described in detail using the following examples, but the chemical reactions described are disclosed in terms of their general applicability to the preparation of the calcium-binding ligands of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, that is, by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily prepared from known starting materials; all temperatures are set forth in degrees Celsius; and, unless otherwise indicated, all parts and percentages are by weight.

Standard amino acids were purchased from Sigma, St. Louis, Mo. Crystals of $Ca^{2+}{}_3\{Boc\text{-}Gly\text{-}Nleu\text{-}Nleu\text{-}O^-\}_6 \cdot 3$ $CH_3CN$ were grown from acetonitrile solutions. Solvent molecules are not shown in FIG. 1. The structure of $Ca^{2+}{}_3$

(Boc-Gly-Nleu-Nleu-O$^-$)$_6$, C$_{57}$H$_{102}$N$_9$O$_{18}$Ca$_{1.5}$·3 CH$_3$CN, F.W.=1384.77, was determined by single crystal X-ray diffraction techniques: Monoclinic P2$_1$/n, a=17.320(8), b=17.802(10), c=26.693(9), β=97.47° (3), Z=4, 10757 unique reflections, 3°<2θ<45°, R=0.0941 for 6429 reflections with F$_o$≧4.0 σ(Fo). All intensity measurements were recorded at 193 K, using graphite-monochromated MoKα radiation (λ=0.71073) at a variable rate ω scan technique. The structure has been solved by direct methods and refined by full-matrix least squares. All calculations were performed using SHELXTL PLUS programs.

EXAMPLE 1

Preparation of Ca$^{2+}$$_3$ (Boc-Gly-Nleu-Nleu-O$^-$)$_6$

The peptoid containing dimer, Boc-Gly-Nleu-OH (Feng, Y. B. (1996) Collagen-Based Biomaterials, University of California, San Diego), was allowed to react with Nleu-OEt using BOP (O-benzotriazolyl-N-oxytri-dimethylamino-phosphonium hexafluorophosphate) as the activating reagent to afford Boc-Gly-Nleu-Nleu-OEt (Scheme 1). The trimer was then saponified with KOH in H$_2$O (containing calcium ions)-THF to afford the calcium ion complex of Boc-Gly-Nleu-Nleu-OH. The calcium ions in the water were sufficient to form the complex.

Scheme 1

Boc-Gly-Nleu-Nleu-OEt

A solution of Boc-Gly-Nleu-OH (26 g, 92 mmol) and HCl*Nleu-OEt (18 g, 92 mmol) was cooled to 0° C. The coupling reagent, BOP (O-benzotriazolyl-N-oxytri-dimethylamino-phosphonium hexafluorophosphate, 41 g, 92 mmol), was then added portion-wise to the solution, followed by the addition of triethylamine (26 mL, 183 mmol). The ice bath was removed and the solution was left stirring overnight. The DMF was removed under reduced pressure and H$_2$O (800 mL) and EtOAc (800 mL) were added. The EtOAc layer was washed with H$_2$O (800 mL), NaHCO$_3$ (2×800 mL), brine (800 mL), 2 N NaHSO$_4$ (2×800 mL), and brine (3×800 mL). The organic layer was dried over anhydrous Na$_2$SO$_4$ and the volatiles were removed by rotary evaporation under reduced pressure to give an oil. Purification via flash chromatography (SiO2, 1/1, hexanes/EtOAc) afforded 28 g (72% yield) of Boc-Gly-Nleu-Nleu-OEt. Rf=0.2 (1/1 hexanes/EtOAc). $^1$H NMR (300 MHz, CDCl$_3$) δ 5.49 (br s, 1H), 4.22–4.01 (m, 8 H), 3.19–3.06 (m, 4 H), 1.93–1.82 (m 2 H), 1.40 (s, 9 H), 1.24 (t, 3 H) 0.85–0.98 (m, 12 H).

FAD-MS: m/z=430 (M+H) calculated for C$_{21}$H$_{39}$N$_3$O$_6$ 429, found 430 (M+H).

Ca$^{2+}$$_3${Boc-Gly-Nleu-Nleu-O$^-$}$_6$

A solution of Boc-Gly-Nleu-Nleu-OEt (4.7 g, 11 mmol), H$_2$O (20 mL), and THF (20 mL) was cooled to 0° C. KOH was dissolved in H$_2$O (6 mL) and was added slowly to the solution. The ice bath was removed and the solution was left stirring at room temperature for 30 min. The THF was then removed under reduced pressure and H$_2$O (30 mL) and EtOAc (80 mL) were added and the EtOAc layer separated. The H$_2$O layer was extracted with EtOAc further (2×80 mL). The EtOAc layers were pooled together and washed with brine (3×120 mL). The solution was then dried over Na$_2$SO$_4$ and the solvent was removed by rotary evaporation. Purification via flash chromatography (SiO$_2$, 1.5/1 EtOAc/MeOH) gave a white powder (4 g). Rf=0.3 (SiO$_2$, 1.5/1 EtOAc/MeOH) Crystals were grown from a smaller portion of this material in acetonitrile solvent for X-ray crystallography.

Characterization of white powder:

$^1$H NMR (300 MHz, DMSO-d$_6$) δ 6.64 (br s, 1 H), 4.14–2.99 (m, 10 H), 1.81–1.76 (m, 2H), 1.35 (s, 9 H), 0.77 –0.86 (m, 12 H). C$_{38}$H$_{68}$CaN$_6$O$_{12}$ [Ca$^{2+}$(Boc-Gly-Nleu-Nleu-O$^-$) fragment, M$^+$]. MS-MALDI: 842 and 864 corresponding to M-(Ca$^{2+}$$_2$ (Boc-Gly-Nleu-Nleu-O$^-$)$_4$+H) and M-(Ca$^{2+}$$_2$ (Boc-Gly-Nleu-Nleu-O$^-$)$_4$+Na), respectively. Anal. Calcd for C$_{114}$H$_{204}$Ca$_3$N18O$_{36}$: C, 54.27, H, 8.15, N, 10.00, Ca, 4.77. Found: C, 54.18; H, 7.86; N, 9.78; Ca, 4.21.

| Structure Determination Summary | |
|---|---|
| Crystal Data | |
| Empirical Formula | C$_{57}$H$_{102}$N$_9$O$_{18}$Ca$_{1.5}$·3CH$_3$CN |
| Color; Habit | colorless glob |
| Crystal size (mm) | 0.4 × 0.7 × 0.7 |
| Crystal System | Monoclinic |
| Space Group | P2$_1$/n |
| Unit Cell Dimensions | a = 17.320(8) Å |
| | b = 17.802(10) Å |
| | c = 26.693(9) Å |
| | β = 97.470(0)° |
| Volume | 8160(7) Å$^3$ |
| Z | 4 |
| Formula weight | 1384.77 |
| Density (calc.) | 1.127 Mg/m$^3$ |
| Absorption Coefficient | 0.174 mm$^{-1}$ |
| F(000) | 2844 |
| Data Collection | |
| Diffractometer Used | Siemens R3in/V |
| Radiation | MoKα(λ = 0.71073Å) |
| Temperature (K.) | 193 |
| Monochromator | Highly oriented graphite crystal |
| 2θ Range | 3.0 to 45.00 |
| Scan Type | Wyckoff |
| Scan Speed in ω | Variable; 5.00 to 10.000/min. |
| Scan Range (ω) | 2.00° |
| Background Measurement | Stationary crystal and stationary counter at beginning and end of scan; each for 25.0% of total scan time |
| Standard Reflections | 3 measured every 197 reflections |
| Index Ranges | −20 ≦ h ≦ 20, −19 ≦ k ≦ 0 |
| | −0 ≦ 1 ≦ 31 |
| Reflections Collected | 11073 |
| Independent Reflections | 10757 (R$_{int}$ = 2.02%) |
| Observed Reflections | 6429 (F > 4.0σ(F)) |
| Absorption Correction | N/A |
| Solution and Refinement | |
| System Used | Siemens SHELXTL PLUS (PC Version) |
| Solution | Direct Methods |
| Refinement Method | Full-Matrix Least-Squares |
| Quantity Minimized | Σw(F$_o$ − F$_c$)$^2$ |
| Absolute Structure | N/A |
| Extinction Correction | N/A |
| Hydrogen Atoms | Riding model, fixed isotropic U |
| Weighting Scheme | w$^{-1}$ = σ$^2$ (F) + 0.0010F$^2$ |
| Number of Parameters Refined | 685 |
| Final R Indices (obs. data) | R = 9.41%, wR = 11.75% |

-continued

Structure Determination Summary

| | |
|---|---|
| R Indices (all data) | R = 14.08%, wR = 24.80% |
| Goodness-of-Fit | 2.23 |
| Largest and Mean δ/σ | 3.213, 0.078 |
| Data-to-Parameter Ratio | 9.4:1 |
| Largest Difference Peak | .055 eÅ$^3$ |
| Largest Difference Hole | −0.90 eÅ$^{−3}$ |

TABLE 1

Atomic/Coordinates (×10$^4$) and equivalent isotropic displacement coefficient (Å$^2$ × 10$^3$)

| | x | y | z | U(eq) |
|---|---|---|---|---|
| Ca(1) | 6184 (1) | 2942 (1) | 5378 (1) | 41 (1) |
| Ca(2) | 5000 | 5000 | 5000 | 54 (1) |
| O(5A) | 8676 (8) | 3066 (7) | 5716 (4) | 65 (3) |
| C(1A) | 8135 | 2620 | 6456 | 65 (3) |
| C(2A) | 9555 | 2488 | 6365 | 65 (3) |
| C(3A) | 8571 | 1718 | 5810 | 65 (3) |
| C(4A) | 8721 | 2479 | 6079 | 65 (3) |
| O(SD) | 8862 (8) | 3116 (7) | 5631 (5) | 67 (3) |
| C(1D) | 8480 | 2539 | 6385 | 67 (3) |
| C(2D) | 9858 | 2501 | 6184 | 67 (3) |
| C(3D) | 8827 | 1756 | 5650 | 67 (3) |
| C(4D) | 8992 | 2484 | 5957 | 67 (3) |
| C(6A) | 8130 (6) | 3235 (6) | 5359 (3) | 58 (4) |
| O(7A) | 7539 (4) | 2854 (3) | 5327 (2) | 54 (2) |
| N(8A) | 8227 (4) | 3841 (5) | 5086 (3) | 64 (3) |
| C(9A) | 7671 (5) | 4069 (5) | 4658 (3) | 55 (3) |
| C(10A) | 8117 (6) | 4338 (5) | 4234 (3) | S2 (3) |
| O(11A) | 8827 (4) | 4388 (4) | 4294 (2) | 66 (3) |
| N(12A) | 7658 (4) | 4516 (4) | 3800 (2) | 45 (3) |
| C(13A) | 8020 (5) | 4636 (3) | 3340 (3) | 61 (4) |
| C(14A) | 7911 | 5443 | 3137 | 65 (4) |
| C(15A) | 8381 | 6008 | 3490 | 86 (5) |
| C(16A) | 8148 | 5497 | 2602 | 112 (6) |
| C(17A) | 6838 (5) | 4367 (4) | 3735 (3) | 44 (3) |
| C(18A) | 6655 (5) | 3550 (5) | 3578 (3) | 39 (3) |
| 6(19A) | 7179 (3) | 3132 (3) | 3493 (2) | 54 (2) |
| N(20A) | 5894 (4) | 3363 (3) | 3505 (2) | 38 (2) |
| C(21A) | 5300 (5) | 3790 (4) | 3730 (3) | 39 (3) |
| C(22A) | 5347 (5) | 3678 (3) | 4301 (3) | 34 (3) |
| O(23A) | 4821 (3) | 4014 (3) | 4505 (2) | 44 (2) |
| O(24A) | 5882 (3) | 3289 (3) | 4522 (2) | 40 (2) |
| C(25A) | 5685 (3) | 2583 (2) | 3382 (1) | 44 (3) |
| C(26A) | 5400 | 2464 | 2816 | 46 (3) |
| C(27A) | 6052 | 2611 | 2489 | 57 (4) |
| C(28A) | 5077 | 1664 | 2724 | 65 (4) |
| C(6B) | 6105 | 1969 | 6507 | 60 (4) |
| O(7B) | 6264 | 2120 | 6097 | 58 (2) |
| N(8B) | 6030 | 2448 | 6897 | 58 (3) |
| C(9B) | 6108 | 3253 | 6806 | 54 (3) |
| C(10B) | 5928 (5) | 3648 (5) | 7281 (3) | 5O (3) |
| O(11B) | 5760 (4) | 3284 (3) | 7647 (2) | 66 (3) |
| N(12B) | 5953 (4) | 4410 (3) | 7269 (2) | 48 (3) |
| C(13B) | 5824 (6) | 4808 (10) | 7718 (7) | 46 (2) |
| C(14B) | 5029 | 5209 | 7656 | 46 (2) |
| C(15B) | 4922 | 5674 | 8127 | 46 (2) |
| C(16B) | 4364 | 4636 | 7546 | 46 (2) |
| C(13E) | 5867 (9) | 4859 (18) | 7723 (10) | 108 (5) |
| C(14E) | 5043 | 4804 | 7879 | 108 (5) |
| C(15E) | 4983 | 5249 | 8366 | 108 (5) |
| C(16E) | 4432 | 5086 | 7451 | 108 (5) |
| C(17B) | 6212 (5) | 4822 (4) | 6853 (3) | 45 (3) |
| C(18B) | 7086 (5) | 4792 (4) | 6875 (3) | 48 (3) |
| O(19B) | 7505 (4) | 4539 (3) | 7245 (2) | 64 (2) |
| N(20B) | 7403 (4) | 5068 (4) | 6467 (3) | 47 (3) |
| C(21B) | 6905 (4) | 5260 (4) | 5999 (3) | 45 (3) |
| C(22B) | 6594 (5) | 4571 (6) | 5689 (4) | 56 (4) |
| O(23B) | 6200 (4) | 4701 (3) | 5260 (2) | 76 (3) |
| O(24B) | 6745 (4) | 3933 (4) | 5872 (3) | 71 (3) |
| O(5C) | 6080 (3) | 1023 (3) | 4249 (2) | 64 (3) |
| C(1C) | 7403 | 1501 | 4338 | 80 (5) |
| C(2C) | 7022 | 287 | 3893 | 105 (6) |
| C(3C) | 7036 | 367 | 4834 | 110 (6) |
| C(4C) | 6876 | 805 | 4334 | 71 (4) |
| C(6C) | 5727 (7) | 1467 (4) | 4561 (3) | 53 (4) |
| O(7C) | 6054 (4) | 1771 (3) | 4938 (2) | 54 (2) |
| N(8C) | 4978 (5) | 1523 (4) | 4394 (3) | 59 (3) |
| C(9C) | 4438 (5) | 1972 (5) | 4659 (3) | 55 (4) |
| C(10C) | 3653 (7) | 1884 (6) | 4394 (5) | 90 (5) |
| O(11X) | 3421 (9) | 1333 (9) | 4124 (6) | 74 (4) |
| O(11Y) | 3620 (7) | 1560 (7) | 3930 (5) | 51 (3) |
| N(12X) | 2973 (10) | 2168 (10) | 4677 (7) | 63 (5) |
| N(12Y) | 3181 (9) | 2339 (9) | 4482 (6) | 47 (4) |
| C(13C) | 2426 (10) | 2400 (11) | 4159 (10) | 115 (5) |
| C(14C) | 1776 | 1913 | 4333 | 115 (5) |
| C(15C) | 981 | 2092 | 4029 | 115 (5) |
| C(16C) | 1966 | 1074 | 4286 | 115 (5) |
| C(13F) | 2186 (17) | 2164 (16) | 4414 (10) | 158 (7) |
| C(14F) | 1804 | 1432 | 4568 | 158 (7) |
| C(15F) | 1124 | 1198 | 4170 | 158 (7) |
| C(16F) | 1520 | 1523 | 5087 | 158 (7) |
| C(17C) | 3213 (7) | 2727 (6) | 5030 (5) | 99 (6) |
| C(18C) | 3400 (7) | 2300 (5) | 5530 (5) | 82 (5) |
| O(19X) | 3481 (8) | 1598 (8) | 5627 (5) | 59 (4) |
| O(19Y) | 3200 (8) | 1628 (8) | 5414 (5) | 63 (4) |
| N(20C) | 3609 (5) | 2713 (4) | 5935 (3) | 68 (4) |
| C(21C) | 3753 (6) | 3516 (5) | 5902 (3) | 57 (4) |
| C(22C) | 4517 (5) | 3722 (5) | 5716 (3) | 49 (3) |
| O(23C) | 4612 (4) | 4420 (3) | 5665 (2) | 65 (3) |
| O(24C) | 4967 (4) | 3215 (3) | 5621 (2) | 51 (2) |
| C(25C) | 3842 (13) | 2293 (20) | 6357 (7) | 105 (5) |
| C(26C) | 3234 | 2326 | 6729 | 105 (5) |
| C(27C) | 3558 | 1994 | 7246 | 105 (5) |
| C(28C) | 2487 | 1910 | 6511 | 105 (5) |
| C(25F) | 4021 (12) | 2397 (18) | 6431 (7) | 96 (5) |
| C(26F) | 3563 | 2289 | 6884 | 96 (5) |
| C(27F) | 4060 | 1889 | 7324 | 96 (5) |
| C(28F) | 2810 | 1843 | 6722 | 96 (5) |
| N(1) | 1806 (7) | 4108 (6) | 4963 (4) | 91 (5) |
| C(2) | 1189 (8) | 4043 (7) | 5058 (4) | 76 (5) |
| C(3) | 406 (7) | 3987 (8) | 5178 (5) | 117 (7) |
| N(4X) | 6465 (11) | 6692 (11) | 7151 (8) | 69 (5) |
| N(4Y) | 6452 (12) | 6823 (13) | 6897 (8) | 85 (7) |
| C(5) | 6789 (7) | 7300 (6) | 7079 (5) | 91 (5) |
| C(6) | 7220 (7) | 8009 (6) | 7135 (4) | 92 (5) |
| N(1H) | 5521 (18) | 7519 (17) | 464 (7) | 514 (34) |
| C(2H) | 5750 | 7481 | 879 | 417 (32) |
| C(3H) | 6039 | 7407 | 1418 | 283 (18) |
| O(5B) | 5790 (6) | 1276 (5) | 6675 (4) | 51 (2) |
| C(1B) | 5323 | 604 | 5903 | 51 (2) |
| C(2B) | 5661 | −54 | 6736 | 51 (2) |
| C(3B) | 6731 | 514 | 6307 | 51 (2) |
| C(4B) | 5878 | 602 | 6403 | 51 (2) |
| O(5E) | 6090 (5) | 1257 (4) | 6667 (3) | 32 (2) |
| C(1E) | 5673 | 575 | 5892 | 32 (2) |
| C(2E) | 6023 | −79 | 6725 | 32 (2) |
| C(3E) | 7077 | 544 | 6309 | 32 (2) |
| C(4E) | 6217 | 591 | 6396 | 32 (2) |
| C(25X) | 8203 | 5013 | 6444 | 100 |
| C(26X) | 8842 | 5610 | 6421 | 82 (9) |
| C(27X) | 8551 | 6400 | 6535 | 82 (9) |
| C(28X) | 9569 | 5411 | 6793 | 82 (9) |
| C(25B) | 8186 | 4914 | 6371 | 100 |
| C(26B) | 8700 | 5622 | 6381 | 82 (9) |
| C(27B) | 8802 | 5995 | 6905 | 82 (9) |
| C(28B) | 9500 | 5425 | 6224 | 82 (9) |
| C(25E) | 8224 (4) | 4969 (4) | 6435 (3) | 59 (4) |
| C(26E) | 8709 | 5697 | 6458 | 90 (5) |
| C(27E) | 9572 | 5530 | 6428 | 68 (4) |
| C(28E) | 8623 | 6136 | 6945 | 68 (4) |

*Equivalent isotropic U defined as one third of the trace of the orthogonalized $U_{ij}$ tensor

TABLE 2

Bond lengths (Å)

| | | | |
|---|---|---|---|
| Ca(1)-Ca(2) | 4.254 (3) | Ca(1)-O(7A) | 2.373 (7) |
| Ca(1)-O(24A) | 2.358 (5) | Ca(1)-O(7B) | 2.404 (4) |
| Ca(1)-C(22B) | 3.074 (11) | Ca(1)-O(24B) | 2.338 (7) |
| Ca(1)-O(7C) | 2.389 (5) | Ca(1)-O(24C) | 2.33S (7) |
| Ca(2)-C(22A) | 3.110 (8) | Ca(2)-O(23A) | 2.194 (S) |
| Ca(2)-C(22B) | 3.205 (9) | Ca(2)-O(23B) | 2.171 (6) |
| Ca(2)-C(22C) | 3.153 (9) | Ca(2)-O(23C) | 2.231 (6) |
| Ca(2)-Ca(1A) | 4.254 (3) | Ca(2)-C(22D) | 3.110 (8) |
| Ca(2)-O(23D) | 2.194 (5) | Ca(2)-C(22E) | 3.205 (9) |
| Ca(2)-O(23E) | 2.171 (6) | Ca(2)-C(22F) | 3.153 (9) |
| Ca(2)-O(23F) | 2.231 (6) | O(5A)-O(5D) | 0.427 (19) |
| O(SD)-C(6A) | 1.393 (16) | C(6A)-O(7A) | 1.223 (12) |
| C(6A)-N(8A) | 1.325 (13) | N(8A)-C(9A) | 1.453 (11) |
| C(9A)-C(10A) | 1.528 (13) | C(10A)-O(11A) | 1.223 (12) |
| C(10A)-N(12A) | 1.354 (11) | N(12A)-C(13A) | 1.466 (11) |
| N(12A)-C(17A) | 1.433 (11) | C(17A)-C(18A) | 1.536 (11) |
| C(18A)-O(19A) | 1.219 (11) | C(18A)-N(20A) | 1.348 (11) |
| N(20A)-C(21A) | 1.468 (11) | N(20A)-C(25A) | 1.462 (7) |
| C(21A)-C(22A) | 1.528 (10) | C(22A)-O(23A) | 1.272 (10) |
| C(22A)-O(24A) | 1.242 (9) | C(6B)-O(5B) | 1.443 (11) |
| C(9B)-C(10B) | 1.517 (9) | C(10B)-O(11B) | 1.239 (11) |
| C(10B)-N(12B) | 1.358 (10) | N(12B)-C(13B) | 1.434 (20) |
| N(12B)-C(13E) | 1.475 (29) | N(12B)-C(17B) | 1.451 (11) |
| C(17B)-C(18B) | 1.508 (13) | C(18B)-O(19B) | 1.232 (10) |
| C(18B)-N(20B) | 1.372 (12) | N(20B)-C(21B) | 1.464 (10) |
| N(20B)-C(25X) | 1.398 (7) | N(20B)-C(25B) | 1.438 (7) |
| N(20B)-C(25E) | 1.447 (11) | C(21B)-C(22B) | 1.536 (13) |
| C(22B)-O(23B) | 1.277 (11) | C(22B)-O(24B) | 1.251 (12) |
| O(5C)-C(6C) | 1.351 (11) | C(6C)-O(7C) | 1.216 (10) |
| C(6C)-N(8C) | 1.319 (14) | N(8C)-C(9C) | 1.479 (13) |
| C(9C)-C(10C) | 1.456 (15) | C(10C)-O(11X) | 1.253 (18) |
| C(10C)-O(11Y) | 1.361 (17) | C(10C)-N(12X) | 1.563 (23) |
| C(10C)-N(12Y) | 1.196 (20) | N(12X)-C(13C) | 1.625 (28) |
| N(12X)-C(13F) | 1.450 (32) | N(12X)-C(17C) | 1.395 (21) |
| N(12Y)-C(13C) | 1.473 (25) | N(12Y)-C(13F) | 1.736 (33) |
| N(12Y)-C(17C) | 1.611 (20) | C(17C)-C(18C) | 1.532 (17) |
| C(18C)-N(20C) | 1.320 (15) | N(20C)-C(21C) | 1.466 (11) |
| N(20C)-C(25C) | 1.3677 (27) | C(21C)-C(22C) | 1.517 (14) |
| C(22C)-O(23C) | 1.263 (10) | C(22C)-O(24C) | 1.241 (11) |
| N(1)-C(2) | 1.136 (18) | C(2)-C(3) | 1.437 (19) |
| N(4X)-N(4Y) | 0.713 (30) | N(4X)-C(5) | 1.246 (23) |
| N(4Y)-C(5) | 1.108 (25) | C(S)-C(6) | 1.463 (15) |
| O(5B)-O(5E) | 0.523 (14) | | |

TABLE 3

Bond angles (°)

| | | | |
|---|---|---|---|
| Ca(2)-Ca(1)-O(7A) | 119.6 (2) | Ca(2)-Ca(1)-O(24A) | 60.4 (1) |
| O(7A)-Ca(1)-O(24A) | 93.4 (2) | Ca(2)-Ca(1)-O(7B) | 133.6 (1) |
| Ca(2)-Ca(1)-C(22B) | 48.6 (2) | O(7B)-Ca(1)-C(22B) | 111.8 (2) |
| Ca(2)-Ca(1)-O(24B) | 68.7 (2) | O(7B)-Ca(1)-O(24B) | 91.8 (2) |
| C(22B)-Ca(1)-O(24B) | 21.7 (2) | Ca(2)-Ca(1)-O(7C) | 128.6 (1) |
| .Ca(2)-Ca(1)-O(24C) | 57.5 (1) | O(7A)-Ca(1)-O(24C) | 164.7 (2) |
| O(24A)-Ca(1)-O(24C) | 96.9 (2) | O(7C)-Ca(1)-O(24C) | 106.7 (2) |
| Ca(1)-Ca(2)-C(22A) | 50.6 (1) | Ca(1)-Ca(2)-O(23A) | 58.7 (1) |
| C(22A)-Ca(2)-O(23A) | 19.4 (2) | Ca(1)-Ca(2)-C(22B) | 46.1 (2) |
| Ca(1)-Ca(2)-O(23B) | 45.7 (2) | C(22B)-Ca(2)-O(23B) | 16.3 (3) |
| Ca(i)-Ca(2)-C(22C) | 52.6 (2) | Ca(1)-Ca(2)-O(23C) | 66.3 (2) |
| C(22C)-Ca(2)-O(23C) | 18.7 (2) | Ca(1)-Ca(2)-Ca(1A) | 180.0 (1) |
| C(22A)-Ca(2)-Ca(1A) | 129.4 (1) | O(23A)-Ca(2)-Ca(1A) | 121.3 (1) |
| C(22B)-Ca(2)-Ca(1A) | 133.9 (2) | O(23B)-Ca(2)-Ca(1A) | 134.3 (2) |
| C(22C)-Ca(2)-Ca(1A) | 127.4 (2) | O(23C)-Ca(2)-Ca(1A) | 113.7 (2) |
| Ca(1)-Ca(2)-C(22D) | 129.4 (1) | Ca(1A)-Ca(2)-C(22D) | 50.6 (1) |
| Ca(1)-Ca(2)-O(23D) | 121.3 (1) | Ca(1A)-Ca(2)-O(23D) | 58.7 (1) |
| C(22D)-Ca(2)-O(23D) | 19.4 (2) | Ca(1)-Ca(2)-C(22E) | 133.9 (2) |
| Ca(1)-Ca(2)-O(23E) | 134.3 (2) | C(22E)-Ca(2)-O(23E) | 16.3 (3) |
| Ca(1)-Ca(2)-C(22F) | 127.4 (2) | Ca(1A)-Ca(2)-C(22F) | 52.6 (2) |
| Ca(1)-Ca(2)-O(23F) | 113.7 (2) | Ca(1A)-Ca(2)-O(23F) | 66.3 (2) |
| C(22F)-Ca(2)-O(23F) | 18.7 (2) | C(4A)-O(5A)-C(6A) | 130.3 (7) |
| O(SA)-C(6A)-O(7A) | 116.8 (10) | O(5D)-C(6A)-O(7A) | 130.6 (10) |
| O(5A)-C(6A)-N(8A) | 117.6 (10) | O(5D)-C(6A)-N(8A) | 103.8 (9) |
| O(7A)-C(6A)-N(8A) | 125.3 (8) | Ca(1)-O(7A)-C(6A) | 141.7 (6) |
| C(6A)-N(8A)-C(9A) | 122.8 (8) | N(8A)-C(9A)-C(10A) | 108.8 (7) |
| C(9A)-C(10A)-O(11A) | 121.5 (8) | C(9A)-C(10A)-N(12A) | 114.1 (8) |
| O(11A)-C(10A)-N(12A) | 124.3 (9) | C(10A)-N(12A)-C(13A) | 118.9 (7) |
| C(10A)-N(12A)-C(17A) | 121.6 (7) | C(13A)-N(12A)-C(17A) | 116.7 (6) |
| N(12A)-C(13A)-C(14A) | 112.7 (4) | N(12A)-C(17A)-C(18A) | 111.9 (7) |
| C(17A)-C(18A)-O(19A) | 119.8 (8) | C(17A)-C(18A)-N(20A) | 115.8 (7) |
| O(19A)-C(18A)-N(20A) | 124.1 (7) | C(18A)-N(20A)-C(21A) | 122.5 (6) |
| C(18A)-N(20A)-C(25A) | 118.3 (6) | C(21A)-N(20A)-C(25A) | 114.7 (6) |
| N(20A)-C(21A)-C(22A) | 112.9 (6) | Ca(2)-C(22A)-C(21A) | 120.7 (5) |
| Ca(2)-C(22A)-O(23A) | 35.1 (3) | C(21A)-C(22A)-O(23A) | 114.7 (6) |

TABLE 3-continued

Bond angles (°)

| | | | |
|---|---|---|---|
| Ca(2)-C(22A)-O(24A) | 109.1 (5) | C(21A)-C(22A)-O(24A) | 119.1 (7) |
| O(23A)-C(22A)-O(24A) | 126.2 (7) | Ca(2)-O(23A)-C(22A) | 125.5 (5) |
| Ca(1)-O(24A)-C(22A) | 131.6 (5) | N(20A)-C(25A)-C(26A) | 113.0 (2) |
| O(7B)-C(6B)-O(5B) | 128.2 | N(8B)-C(6B)-O(SB) | 102.7 |
| Ca(1)-O(7B)-C(6B) | 150.9 (1) | N(8B)-C(9B)-C(10B) | 106.4 (3) |
| C(9B)-C(10B)-O(11B) | 120.7 (7) | C(9B)-C(10B)-N(12B) | 115.7 (7) |
| O(11B)-C(10B)-N(12B) | 123.6 (8) | C(10B)-N(12B)-C(13B) | 117.8 (9) |
| C(10B)-N(12B)-C(17B) | 122.4 (7) | C(13B)-N(12B)-C(17B) | 119.2 (9) |
| N(12B)-C(13B)-C(14B) | 111.9 (5) | N(12B)-C(17B)-C(18B) | 111.2 (6) |
| C(17B)-C(18B)-O(19B) | 121.8 (8) | C(17B)-C(18B)-N(20B) | 117.3 (7) |
| O(19B)-C(18B)-N(20B) | 120.9 (8) | C(18B)-N(20B)-C(21B) | 120.6 (7) |
| C(18B)-N(20B)-C(25B) | 123.8 (6) | C(21B)-N(20B)-C(25B) | 110.9 (6) |
| N(20B)-C(21B)-C(22B) | 113.4 (7) | Ca(1)-C(22B)-Ca(2) | 85.3 (2) |
| Ca(1)-C(22B)-C(21B) | 162.0 (6) | Ca(2)-C(22B)-C(21B) | 109.5 (5) |
| Ca(1)-C(22B)-O(23B) | 81.3 (6) | Ca(2)-C(22B)-O(23B) | 28.5 (4) |
| C(21B)-C(22B)-O(23B) | 116.5 (8) | Ca(1)-C(22B)-O(24B) | 43.8 (5) |
| Ca(2)-C(22B)-O(24B) | 124.1 (6) | C(21B)-C(22B)-O(24B) | 118.4 (8) |
| O(23B)-C(22B)-O(24B) | 125.1 (9) | Ca(2)-O(23B)-C(22B) | 135.1 (6) |
| Ca(1)-O(24B)-C(22B) | 114.5 (6) | C(4C)-O(5C)-C(6C) | 124.7 (5) |
| O(5C)-C(6C)-O(7C) | 124.8 (10) | O(SC)-C(6C)-N(8C) | 109.8 (7) |
| O(7C)-C(6C)-N(8C) | 125.4 (9) | Ca(1)-O(7C)-C(6C) | 143.0 (5) |
| C(6C)-N(8C)-C(9C) | 122.3 (7) | N(8C)-C(9C)-C(10C) | 108.6 (8) |
| C(18C)-N(20C)-C(21C) | 121.8 (9) | C(18C)-N(20C)-C(25C) | 113.0 (15) |
| C(21C)-N(20C)-C(25C) | 123.5 (15) | N(20C)-C(21C)-C(22C) | 115.0 (8) |
| Ca(2)-C(22C)-C(21C) | 133.1 (6) | Ca(2)-C(22C)-O(23C) | 34.5 (4) |
| C(21C)-C(22C)-O(23C) | 113.9 (8) | Ca(2)-C(22C)-O(24C) | 100.2 (6) |
| C(21C)-C(22C)-O(24C) | 119.3 (8) | O(23C)-C(22C)-O(24C) | 126.8 (9) |
| Ca(2)-O(23C)-C(22C) | 126.8 (6) | Ca(1)-O(24C)-C(22C) | 145.3 (6) |
| N(20C)-C(25C)-C(26C) | 110.8 (11) | N(1)-C(2)-C(3) | 178.2 (14) |
| N(4Y)-N(4X)-C(5) | 62.0 (23) | N(4X)-N(4Y)-C(5) | 83.3 (25) |
| N(4X)-C(5)-N(4Y) | 34.7 (15) | N(4X)-C(5)-C(6) | 165.4 (15) |
| N(4Y)-C(5)-C(6) | 160.0 (17) | C(6B)-O(5B)-C(4B) | 119.6 |

TABLE 4

Anisotropic displacement coefficients ($A^2 \times 10^3$)

| | $U_{11}$ | $U_{22}$ | $U_{33}$ | $U_{12}$ | $U_{13}$ | $U_{23}$ |
|---|---|---|---|---|---|---|
| Ca(1) | 69 (1) | 28 (1) | 25 (1) | −3 (1) | −4 (1) | −1 (1) |
| Ca(2) | 71 (2) | 46 (2) | 42 (1) | −1 (1) | 3 (1) | −2 (1) |
| C(6A) | 64 (7) | 69 (7) | 34 (5) | 8 (6) | −18 (5) | −12 (5) |
| O(7A) | 69 (5) | 51 (4) | 39 (3) | 5 (3) | −6 (3) | −6 (3) |
| N(8A) | 61 (6) | 8S (6) | 40 (4) | −12 (5) | −19 (4) | 13 (4) |
| C(9A) | 44 (6) | 72 (6) | 48 (5) | −3 (5) | −2 (4) | 0 (5) |
| C(10A) | 54 (7) | 56 (6) | 45 (5) | −6 (5) | 7 (5) | −6 (4) |
| O(11A) | 44 (4) | 90 (5) | 63 (4) | −10 (4) | 4 (3) | −3 (4) |
| N(12A) | 4S (5) | 50 (4) | 41 (4) | −5 (4) | 10 (3) | −5 (3) |
| C(13A) | 75 (7) | 71 (7) | 41 (5) | −14 (6) | 25 (5) | −2 (5) |
| C(14A) | 64 (7) | 77 (7) | 56 (6) | −20 (6) | 14 (5) | 8 (5) |
| C(15A) | 112 (10) | 74 (8) | 72 (7) | −29 (7) | 8 (7) | −3 (6) |
| C(16A) | 169 (13) | 112 (10) | 58 (7) | −61 (10) | 28 (8) | 6 (7) |
| C(17A) | 56 (6) | 41 (5) | 35 (4) | −3 (4) | 1 (4) | −2 (4) |
| C(18A) | 45 (6) | 46 (5) | 25 (4) | 4 (5) | 5 (4) | −1 (4) |
| O(19A) | 51 (4) | S7 (4) | 53 (4) | 4 (3) | 5 (3) | −2 (3) |
| N(20A) | 49 (5) | 35 (4) | 28 (3) | −2 (3) | 3 (3) | −3 (3) |
| C(21A) | 48 (5) | 40 (5) | 27 (4) | 2 (4) | 3 (4) | 2 (4) |
| C(22A) | 45 (5) | 28 (4) | 36 (4) | 0 (4) | 4 (4) | −1 (4) |
| O(23A) | 52 (4) | 44 (3) | 35 (3) | 5 (3) | 5 (3) | −1 (3) |
| O(24A) | 58 (4) | 35 (3) | 24 (3) | 7 (3) | −1 (3) | 0 (2) |
| C(25A) | 61 (6) | 34 (4) | 37 (4) | −3 (4) | 6 (4) | 5 (4) |
| C(26A) | 53 (6) | 46 (5) | 37 (4) | −2 (4) | −1 (4) | −8 (4) |
| C(27A) | 73 (7) | 62 (6) | 39 (5) | 5 (5) | 13 (5) | −7 (4) |
| C(28A) | 80 (8) | 46 (6) | 68 (6) | −2 (5) | 5 (5) | −18 (5) |
| C(6B) | 95 (8) | 32 (5) | 50 (6) | −5 (5) | −4 (5) | 8 (5) |
| O(7B) | 113 (6) | 29 (3) | 30 (3) | −5 (3) | −6 (3) | 7 (3) |
| N(8B) | 107 (7) | 22 (4) | 45 (4) | 3 (4) | 6 (4) | −4 (3) |
| C(9B) | 90 (8) | 25 (4) | 43 (5) | 1 (5) | −6 (5) | −1 (4) |
| C(10B) | 64 (7) | 37 (5) | 44 (5) | 3 (5) | −9 (5) | 0 (4) |
| O(11B) | 116 (6) | 32 (3) | 51 (4) | −4 (4) | 9 (4) | 0 (3) |
| N(12B) | 71 (5) | 30 (4) | 40 (4) | 1 (4) | 0 (4) | |
| C(17B) | 52 (6) | 32 (5) | 47 (5) | −5 (4) | −10 (4) | −1 (4) |
| C(18B) | 58 (6) | 31 (5) | 52 (5) | −6 (4) | −7 (5) | O (4) |
| O(19B) | 62 (4) | 61 (4) | 63 (4) | 4 (3) | −21 (3) | 15 (3) |

TABLE 4-continued

Anisotropic displacement coefficients (A² × 10³)

| | $U_{11}$ | $U_{22}$ | $U_{33}$ | $U_{12}$ | $U_{13}$ | $U_{23}$ |
|---|---|---|---|---|---|---|
| N(20B) | 49 (5) | 35 (4) | S0 (4) | −5 (4) | −10 (4) | −5 (3) |
| C(21B) | 56 (6) | 41 (5) | 35 (4) | −3 (4) | −9 (4) | −6 (4) |
| C(22B) | 40 (6) | 66 (7) | 62 (6) | 2 (5) | 3 (5) | −27 (5) |
| O(23B) | 56 (4) | 110 (6) | 57 (4) | 8 (4) | −7 (4) | −44 (4) |
| O(24B) | 75 (5) | 47 (4) | 89 (5) | −3 (4) | 4 (4) | |
| O(5C) | 94 (6) | 46 (4) | 48 (4) | −5 (4) | 2 (4) | −12 (3) |
| C(1C) | 97 (9) | 65 (7) | 72 (7) | 10 (6) | −13 (6) | −4 (6) |
| C(2C) | 155 (13) | 88 (9) | 74 (8) | 21 (8) | 23 (8) | −36 (7) |
| C(3C) | 185 (14) | 65 (8) | 78 (8) | 48 (8) | 7 (9) | 11 (6) |
| C(4C) | 108 (10) | 46 (6) | 58 (6) | 15 (6) | 3 (6) | −5 (5) |
| C(6C) | 99 (9) | 24 (4) | 34 (5) | −11 (5) | S (5) | −1 (4) |
| O(7C) | 96 (5) | 28 (3) | 34 (3) | −1 (3) | −6 (3) | −1 (3) |
| N(8C) | 84 (7) | 46 (5) | 46 (4) | −16 (5) | 7 (5) | −6 (4) |
| C(9C) | 76 (7) | 41 (5) | 49 (5) | −16 (5) | 5 (5) | −9 (4) |
| C(10C) | 103 (10) | 47 (6) | 106 (9) | 9 (6) | −38 (8) | −34 (6) |
| C(17C) | 103 (10) | 58 (7) | 125 (11) | 24 (7) | −31 (8) | −44 (7) |
| C(18C) | 93 (9) | 27 (5) | 129 (11) | −2 (6) | 29 (8) | −10 (6) |
| N(20C) | 88 (7) | 37 (5) | 83 (6) | −7 (4) | 30 (5) | 6 (4) |
| C(21C) | 78 (7) | 41 (5) | 54 (6) | −1 (5) | 19 (5) | 2 (4) |
| C(22C) | 80 (8) | 38 (5) | 28 (4) | −11 (5) | 3 (5) | 1 (4) |
| O(23C) | 109 (6) | 31 (3) | 58 (4) | −19 (4) | 25 (4) | −6 (3) |
| O(24C) | 70 (5) | 44 (4) | 41 (3) | −6 (3) | 12 (3) | 0 (3) |
| N(1) | 95 (8) | 95 (8) | 86 (7) | 15 (7) | 18 (7) | −13 (6) |
| C(2) | 80 (9) | 89 (8) | 59 (7) | S (8) | 7 (7) | −14 (6y |
| C(3) | 94 (11) | 158 (14) | 98 (10) | −5 (10) | 12 (8) | −10 (9.) |
| C(5) | 68 (8) | 59 (7) | 141 (11) | 2 (6) | −9 (8) | −48 (8). |
| C(6) | 97 (9) | 68 (7) | 100 (9) | −11 (7) | −31 (7) | −12 (7) |
| N(1H) | 575 (66) | 288 (41) | 741 (64) | 40 (39) | 319 (51) | 106 (42) |
| C(2H) | 242 (38) | 79 (15) | 1012 (85) | 15 (21) | 392 (50) | 89 (40) |
| C(3H) | 183 (23) | 511 (46) | 144 (18) | −63 (26) | −22 (16) | −58 (24) |
| C(25E) | 53 (6) | 49 (6) | 72 (6) | 1 (5) | −1 (5) | −3 (5) |
| C(26E) | 65 (8) | 84 (9) | 121 (10) | −6 (7) | 18 (7) | −12 (8) |

The anisotropic displacement exponent takes the form: $-\pi^2 (h^2 a^{*2} U_{11} + \ldots + 2hka^*b^* U_{12})$

TABLE 5

H-Atom coordinates (×10⁴) and isotropic displacement coefficients (Å² × 10³)

| | x | y | z | U |
|---|---|---|---|---|
| HH(1AA) | 7616 | 2614 | 6280 | 65 (3) |
| HH(1AB) | 8187 | 2233 | 6709 | 65 (3) |
| H(1AC) | 8238 | 3100 | 6615 | 65 (3) |
| H(2AA) | 9650 | 2962 | 6.533 | 65 (3) |
| H(2AB) | 9611 | 2091 | 6610 | 65 (3) |
| H(2AC) | 9923 | 2418 | 6129 | 65 (3) |
| H(3AA) | 8053 | 1710 | 5633 | 65 (3) |
| H(3AB) | 8940 | 1647 | 5576 | 65 (3) |
| H(3AC) | 8628 | 1321 | 6056 | 65 (3) |
| H(1DA) | 7941 | 2528 | 6244 | 67 (3) |
| H(1DB) | 8589 | 2122 | 6611 | 67 (3) |
| H(1DC) | 8590 | 3000 | 6567 | 67 (3) |
| H(2DA) | 9963 | 2955 | 6376 | 67 (3) |
| H(2DB) | 9970 | 207S | 6402 | 67 (3) |
| H(2DC) | 10179 | 2484 | 5917 | 67 (3) |
| H(3DA) | 8288 | 1744 | 55o8 | 67 (3) |
| H(3DB) | 9148 | 1740 | 5383 | 67 (3) |
| H(3DC) | 8939 | 1330 | 5868 | 67 (3) |
| H(8AA) | 8658 | 4121 | 5165 | 70 |
| H(9AA) | 7346 | 4464 | 4757 | 70 |
| H(9AB) | 7346 | 3650 | 4543 | 70 |
| H(13A) | 7793 | 4292 | 3086 | 70 |
| H(13B) | 8567 | 4527 | 3406 | 70 |
| H(14A) | 7369 | 5571 | 3118 | 70 |
| H(15A) | 8302 | 6505 | 3354 | 70 |
| H(15B) | 8210 | 5988 | 3818 | 70 |
| H(15C) | 8924 | 5883 | 3519 | 70 |
| H(16A) | 8077 | 6003 | 2480 | 70 |
| H(16B) | 8685 | 5357 | 2612 | 70 |
| H(16C) | 7830 | 5163 | 2380 | 70 |
| H(17A) | 6583 | 4699 | 3482 | 70 |
| H(17B) | 6635 | 4468 | 4046 | |
| H(21A) | 4793 | 3642 | 3572 | 70 |
| H(21B) | 5365 | 4313 | 3659 | 70 |
| H(25A) | 5281 | 2433 | 3575 | 70 |
| H(25B) | 6127 | 2264 | 3478 | 70 |
| H(26A) | 4985 | 2813 | 2718 | 70 |
| H(27A) | 5855 | 2S32 | 2140 | 70 |
| H(27B) | 6230 | 3119 | 2536 | 70 |
| H(27C) | 6476 | 2272 | 2586 | 70 |
| H(28A) | 4901 | 1598 | 2371 | 70 |
| H(28B) | 5479 | 1305 | 2830 | 70 |
| H(28C) | 4649 | 1589 | 2914 | 70 |
| H(9BA) | 5749 | 3408 | 6521 | 80 |
| H(9BB) | 6629 | 3359 | 6741 | 80 |
| H(13A) | 6232 | 5174 | 7781 | 80 |
| H(13B) | 5858 | 4478 | 8004 | 80 |
| H(14A) | 5009 | 5544 | 7372 | 80 |
| H(15A) | 4423 | 5918 | 8078 | 100 |
| H(1SB) | 4950 | 5350 | 8416 | 100 |
| H(15C) | 5325 | 6047 | 8182 | 100 |
| H(16A) | 3873 | 4894 | 7508 | 100 |
| H(16B) | 4420 | 4369 | 7240 | 100 |
| H(16C) | 4384 | 4287 | 7821 | 100 |
| H(13C) | 5989 | 5379 | 7678 | 80 |
| H(13D) | 6235 | 4665 | 7992 | 80 |
| H(14B) | 4937 | 4285 | 7941 | 80 |
| H(15D) | 4466 | 5204 | 8454 | 100 |
| H(1SE) | 5349 | 5051 | 8635 | 100 |
| H(15F) | 5099 | 5768 | 8313 | 100 |

TABLE 5-continued

H-Atom coordinates (×10⁴) and isotropic displacement coefficients (Å² ×10³)

| | x | y | z | U |
|---|---|---|---|---|
| H(16D) | 3923 | 5048 | 7553 | 100 |
| H(16E) | 4539 | 5601 | 7376 | 100 |
| H(16F) | 4455 | 4786 | 7154 | 100 |
| H(17A) | 6048 | 5336 | 6866 | 80 |
| H(17B) | 5974 | 4609 | 6540 | 80 |
| H(21A) | 7204 | 5558 | 5794 | 80 |
| H(21B) | 6478 | S563 | 6078 | 80 |
| H(1CA) | 7313 | 1825 | 4613 | 100 |
| H(1CB) | 7939 | 1347 | 4380 | 100 |
| H(1CC) | 7286 | 1767 | 4024 | 100 |
| H(2CA) | 6923 | 559 | 3580 | 100 |
| H(2CB) | 7554 | 120 | 3941 | 100 |
| H(2CC) | 6682 | −139 | 3882 | 100 |
| H(3CA) | 6945 | 687 | 5109 | 100 |
| H(3CB) | 6695 | −60 | 4823 | 100 |
| H(3CC) | 7567 | 199 | 4882 | 100 |
| H(9CA) | 4587 | 2492 | 4669 | 80 |
| H(9CB) | 4454 | 1793 | 4999 | 80 |
| H(13A) | 2519 | 2272 | 3823 | 115 (5) |
| H(13B) | 2306 | 2925 | 4173 | 115 (5) |
| H(14A) | 1745 | 2021 | 4682 | 115 (5) |
| H(15A) | 588 | 1781 | 4145 | 115 (5) |
| H(15B) | 857 | 2611 | 4074 | 115 (5) |
| H(15C) | 1003 | 1996 | 3677 | 115 (5) |
| H(16A) | 1556 | 777 | 4396 | 115 (5) |
| H(16B) | 2013 | 957 | 3940 | 115 (5) |
| H(16C) | 2448 | 962 | 4493 | 115 (5) |
| H(13A) | 2596 | 2039 | 4218 | 158 (7) |
| H(13B) | 1805 | 2452 | 4203 | 158 (7) |
| H(14A) | 2188 | 1040 | 4593 | 158 (7) |
| H(15A) | 897 | 742 | 4275 | 158 (7) |
| H(15B) | 737 | 1587 | 4135 | 158 (7) |
| H(15C) | 1312 | 1118 | 3851 | 158 (7) |
| H(16A) | 1284 | 1063 | 5178 | 158 (7) |
| H(16B) | 1955 | 1640 | 5336 | 158 (7) |
| H(16C) | 1146 | 1922 | 5072 | 158 (7) |
| H(17A) | 2766 | 3041 | 5047 | 80 |
| H(17B) | 3650 | 3046 | 4996 | 80 |
| H(21A) | 3750 | 3730 | 6232 | 80 |
| H(21B) | 3336 | 3741 | 5680 | 80 |
| H(25A) | 4280 | 2593 | 6494 | 80 |
| H(25D) | 4021 | 1783 | 6346 | 80 |
| H(26A) | 3104 | 2844 | 6777 | 80 |
| H(27A) | 3168 | 2022 | 7469 | 100 |
| H(27B) | 3700 | 1479 | 7204 | 100 |
| H(27C) | 4009 | 2274 | 7386 | 100 |
| H(28A) | 2114 | 1936 | 6747 | 100 |
| H(28B) | 2273 | 2141 | 6198 | 100 |
| H(28C) | 2607 | 1394 | 6452 | 100 |
| H(25B) | 4507 | 2642 | 6543 | 80 |
| H(25C) | 4133 | 1916 | 6296 | 80 |
| H(26B) | 3422 | 2775 | 6998 | 80 |
| H(27E) | 3760 | 1829 | 7599 | 100 |
| H(27F) | 4214 | 1405 | 7214 | 100 |
| H(27G) | 4514 | 2185 | 7432 | 100 |
| H(28E) | 2532 | 1780 | 7007 | 100 |
| H(28F) | 2492 | 2112 | 6461 | 100 |
| H(28G) | 2940 | 1359 | 6597 | 100 |
| H(3A) | 314 | 3508 | 5324 | 100 |
| H(3B) | 312 | 4379 | 5409 | 100 |
| H(3C) | 61 | 4048 | 4868 | 100 |
| H(6A) | 7455 | 8134 | 6839 | 100 |
| H(6B) | 6859 | 8396 | 7198 | 100 |
| H(6C) | 7617 | 7966 | 7420 | 100 |
| H(1BA) | 5456 | 1011 | 5695 | 51 (2) |
| H(1BB) | 5369 | 137 | 5730 | 51 (2) |
| H(1BC) | 4797 | 665 | 5973 | 51 (2) |
| H(2BA) | 5129 | −1 | 6796 | 51 (2) |
| H(2BB) | 5723 | −522 | 6567 | 51 (2) |
| H(2BC) | 5995 | −47 | 7052 | 51 (2) |
| H(3BA) | 6868 | 921 | 6100 | 51 (2) |
| H(3BB) | 7065 | 521 | 6624 | 51 (2) |
| H(3BC) | 6793 | 46 | 6138 | 51 (2) |
| H(1EA) | 5792 | 991 | 5686 | 32 (2) |
| H(1EB) | 5746 | 113 | 5718 | 32 (2) |
| H(1EC) | 5142 | 611 | 5956 | 32 (2) |
| H(2EA) | 5487 | −52 | 6779 | 32 (2) |
| H(2EB) | 6113 | −541 | 6555 | 32 (2) |
| H(2EC) | 6349 | −61 | 7044 | 32 (2) |
| H(3EA) | 7199 | 960 | 6104 | 32 (2) |
| H(3EB) | 7403 | 562 | 6629 | 32 (2) |
| H(3EC) | 7166 | 82 | 6140 | 32 (2) |
| H(25B) | 8310 | 4693 | 6138 | 68 (4) |
| H(25C) | 8404 | 4665 | 6723 | 68 (4) |
| H(26B) | 8514 | 6005 | 6174 | 68 (4) |
| H(27D) | 9859 | 5992 | 6443 | 68 (4) |
| H(27E) | 9775 | 5214 | 6705 | 68 (4) |
| H(27F) | 9621 | 5279 | 6115 | 68 (4) |
| H(28D) | 8927 | 6587 | 6954 | 68 (4) |
| H(28E) | 8085 | 6262 | 6950 | 68 (4) |
| H(28F) | 8802 | 5831 | 7233 | 68 (4) |

The above described preferred calcium complexes of the invention, having novel glycyl-dipeptoid ligands as well as novel glycyl-peptide-peptoid ligands, each possessing three oxygen coordination sites, has applications in coordination chemistry and also for the design of new calcium ionophores. The use of these ionophores can probe the mechanism of ion transport through membranes and are means by which $Ca^{2+}$ can be introduced into biological cells and organelles and its rate of influx controlled. Such ionophores are also useful as time release storage depots in addition to having the ability to treat disease states by the alteration of membrane permeability. There will be various modifications, improvements and applications of the disclosed invention that will be apparent to those skilled in the art, and the present application is intended to cover such embodiments. Although the present invention has been described in terms of certain preferred embodiments, it is intended that the full scope of the disclosure be measured only by reference to the following claims.

What is claimed is:

1. A chemical complex comprising three divalent metal ions selected from the group consisting of $Ca^{2+}$, $Mg^{2+}$, $Fe^{2+}$ and $Mn^{2+}$ and six linear, N-protected peptide-peptoid trimers.

2. A chemical complex consisting of three divalent metal ions selected from the group consisting of $Ca^{2+}$, $Mg^{2+}$, $Fe^{2+}$ and $Mn^{2+}$ coordinated to six linear, N-protected peptide-peptoid trimers wherein solvent molecules are not bound at the coordination sites.

3. A chemical complex according to claim 1 comprising at least two species of linear N-protected peptide-peptoid trimers.

4. A chemical complex according to any one of claims 1, 2 or 3 wherein the peptoid residues are N-substituted isomers of amino acids selected from the group consisting of glycine, valine, leucine, isoleucine, glutamine, lysine, phenylalanine and aspartic acid.

5. A chemical complex according to claim 1 wherein the N-protected peptide-peptoid trimer is a Boc-Gly-AA-peptoid, a Boc-Gly-peptoid-AA or a Boc-Gly-dipeptoid, wherein the peptoid is selected from the group consisting of N-substituted isomers of glycine, valine, leucine, isoleucine, glutamine, lysine, phenylalanine, and aspartic acid.

6. A chemical complex according to claim 1 comprising three divalent metal ions selected from the group consisting of $Ca^{2+}$, $Mg^{2+}$, $Fe^{2+}$ and $Mn^{2+}$ and six linear, N-protected Gly-dipeptoid trimers.

7. A chemical complex according to claim 6 wherein the peptide-dipeptoid trimers are Gly-Nleu-Nleu.

8. A chemical complex according to claim 1 comprising three divalent metal ions selected from the group consisting of $Ca^{2+}$, $Mg^{2+}$, $Fe^{2+}$ and $Mn^{2+}$ and six linear, N-protected dipeptide-peptoid trimers.

9. A chemical complex according to claim 8 wherein the dipeptide-peptoid trimers are Gly-Pro-Nleu or Gly-Nleu-Pro.

10. A chemical complex according to claim 1 comprising N-protected dipeptide-peptoid trimers selected from the group consisting of Boc-Gly-Pro-Nleu-O⁻

Boc-Gly-Nleu-Pro-O⁻

Boc-Gly-AA-Nleu-O⁻; and

Boc-Gly-Nleu-AA-O⁻ wherein AA is any selected substituted or unsubstituted α-amino acid residue whether naturally occurring or synthetic.

11. A chemical complex according to claim 1 of the formula $Ca^{2+}_3(Boc\text{-}Gly\text{-}Pro\text{-}Nleu\text{-}O^-)_6$ or $Ca^{2+}_3(Boc\text{-}Gly\text{-}Nleu\text{-}Pro\text{-}O^-)_6$.

12. A chemical complex according to claim 1 of the formula $M^{2+}_3(Boc\text{-}Gly\text{-}Nleu\text{-}Nleu\text{-}O)_6$, wherein $M^{2+}$ is a divalent metal ion selected from the group consisting of $Ca^{2+}$, $Mg^{2+}$, $Fe^{2+}$ or $Mn^{2+}$ and Nleu is N-isobutylglycine.

13. A calcium complex according to claim 1 of the formula $Ca^{2+}_3(Boc\text{-}Gly\text{-}Nleu\text{-}Nleu\text{-}O)_6$, wherein Nleu is N-isobutylglycine.

14. A chemical complex according to claim 1 having a globular centrosymmetric conformation, comprising three divalent metal ions and six N-protected peptide-peptoid trimers, wherein said divalent metal ions are in the central core of the globular complex, and the anionic carboxylate regions of said N-protected peptide-peptoid trimers face inwardly and the hydrophobic portions of said N-protected peptide-peptoid trimers face outwardly.

15. A chemical complex according to claim 1 having a globular centrosymmetric conformation, comprising three $Ca^{++}$ ions and six N-protected peptide-peptoid trimers, wherein said calcium ions are in the central core of the globular complex, and the anionic carboxylate regions of said N-protected peptide-peptoid trimers face inwardly and the hydrophobic portions of said N-protected peptide-peptoid trimers face outwardly.

16. A chemical complex according to claim 15 wherein one of said calcium ions is located at the center of symmetry and two of said calcium ions are located lateral thereto, and said central calcium ion is coordinated to six peptide-peptoid trimers through C-terminal carboxylate oxygens thereof and each said lateral calcium ions is coordinated to three of said peptoid-peptide trimers both through a carboxylate oxygen and a urethane oxygen thereof.

17. A chemical complex according to claim 15 wherein the six trimers are Boc-Gly-Nleu-Nleu-O and each trimer is coordinated to a lateral calcium ion through a first carboxylate oxygen and a urethane carbonyl oxygen and each said trimer is coordinated to the central calcium ion through a second carboxylate ion.

18. A chemical complex according to claim 16 or 17 having the formula $Ca^{2+}_3(Boc\text{-}Gly\text{-}Nleu\text{-}Nleu\text{-}O)_6$, wherein Nleu is N-isobutylglycine.

19. A complex according to claim 15 or 16 wherein one side of the globular complex consists of structures of left-handed helicity and the opposite side consists of structures of right-handed helicity.

20. A chemical complex according to claim 1 wherein the N-protecting group is a hydrophobic moiety selected from the group consisting of $C_6$–$C_{24}$ alkyl groups, aromatic groups such as benzyl and conventional peptide blocking groups such as t-butyloxycarbonyl (tBoc), benzyloxycarbonyl, biphenylylisopropyloxycarbonyl (Bpoc), triphenylmethyl (trityl), 9-fluorenylmethyloxycarbonyl (Fmoc) and p-toluenesulfonyl groups.

21. A complex according to claim 1 wherein the side chains of the residues in each said linear N-protected peptide-peptoid trimer are achiral.

22. A complex according to claim 1 wherein the side chains of the residues in each said linear N-protected peptide-peptoid unit are chiral.

* * * * *